US005989543A

United States Patent [19]
Davidé et al.

[11] Patent Number: 5,989,543
[45] Date of Patent: Nov. 23, 1999

[54] MYCONEMATICIDES AND METHODS FOR USING THE SAME

[75] Inventors: Romulo Davidé, Los Banos, Philippines; Keith Leslie Williams, New South Wales, Australia

[73] Assignee: The Australian Technological Innovation Corporation Pty. Ltd., Glebe, Australia

[21] Appl. No.: 08/760,384

[22] Filed: Dec. 4, 1996

Related U.S. Application Data

[63] Continuation of application No. 08/400,539, Mar. 8, 1995, abandoned, and a continuation of application No. 07/838,249, Mar. 3, 1992, abandoned, and a continuation of application No. PCT/AU90/00325, Aug. 2, 1990.

[30] Foreign Application Priority Data

Aug. 3, 1989 [AU] Australia .................................. PJ5591
Oct. 30, 1989 [AU] Australia .................................. PJ7124

[51] Int. Cl.$^6$ .............................. A01N 63/00; C12N 1/14
[52] U.S. Cl. ........................................ 424/93.5; 435/254.1
[58] Field of Search ........................ 424/93.5; 435/254.1

[56] References Cited

U.S. PATENT DOCUMENTS

| 4,282,327 | 8/1981 | Hanka et al. | 435/932 |
|---|---|---|---|
| 4,751,082 | 6/1988 | Schaerffenberg et al. | 424/93 |
| 4,837,313 | 6/1989 | Tomura et al. | 536/55.1 |
| 4,840,903 | 6/1989 | Wu | 435/932 |
| 4,900,348 | 2/1990 | Hoitink | 435/254 |
| 4,942,030 | 7/1990 | Osborne | 435/254 |
| 4,985,364 | 1/1991 | Hildebrand et al. | 435/254 |
| 5,068,105 | 11/1991 | Lewis et al. | 435/254 |
| 5,360,607 | 11/1994 | Eyal et al. | 424/93.5 |

OTHER PUBLICATIONS

Hewlett, T.E et al., "J. Nematology," vol. 20, #4, p. 578–584, 1988.
Derwent Abstract Accession No: C88–116934.
Derwent Abstract Accession No.: C86–092546.
Derwent Abstract Accession No. C82–F44831.
Japio Accession No. 88–192377.
Japio Accession No. 86–146195.
Japio Accession No. 82–067543.
Biotechnology Abstract Accession No. 88–12031.
Biotechnology Abstract Accession No. 86–11255.
Jatala (1986) Annual Reviews of Phytopathology 24, pp. 453–489.
Reddy et al. (1989) Pak J Nematol 7(1), pp. 55–60. Abstract.
Hewlett et al (1988) J. Nematol 20(4), pp. 578–584.
Sayre (1986) Crop Prot 5(4), pp. 268–276.
1. Cabinillas E & Barker KR (1989) J Nematol 21:115–120 Impact of *Paecilomyces lilacinus* inoculum level and application time on control of *Moidogyne incognita* on tomato.
2. Cabanilas E, Barker KR & Kaykin ME (1988) J.Nematol. 20:362–365. Histology of the interactions of *Paecilomyces lilacinus* with *Meloidogyne icognita* on tomato.
3. Cabanillas E, Barker KR & Nelson LA (1989) J. Nematol. 21:121–130. Survival of *Paecilomyces lilacinus* in selected carriers and related effects on *Meloidogyne icognita* on tomato.
4. Cabanillas E, Barker KR & Nelson LA (1989) J.Nematol. 21:164–172. Growth of isolates of *Paecilomyces lilacinus* and their efficacy in biocontrol of *Meloidogyne incognita* on tomato.
5. Cayrol J–C, Djian C & Pijarowski L (1989) Revue Nematol 12:331–336. Study of the nematocidal properties of the culture filtrate of the nematophagous fungus *Paecilomyces lilacinus*.
7. Davide RG (1982) Unpublished SEARCA Professional Chair Lecture, UPLB, Los Banos, Phillippines. Recent advances in cultural and biological control of nematodes.
8. Davide RG (1987) Phil. Phytopath.23:18–21. Biological control of nematodes using *Paecilomyces lilacinus* in the Phillipines.
9. Davide RG (1988) J. Nematol. 20:214–218. Nematode problems affecting agriculture in the Phillipines.
10. Davide RG & Batino E (1985) Phil Agr 68:159–167. Biological control of root–knot nematodes on cotton through the use of fungi *Paecilomyces lilacinus* (thom) samson and *Gliocladium roseum* banier as seed treatment.
12. Davide RG & Zorilla RA (1985) Phil Agr 68:493–500, Evaluation of a fungus *Paecilomyces lilacinus* for the biological control or root–knot nematodes *Meloidogyne incognita* on okra as compared with nematicide izazofos.
14. Davide RG & Zorilla RA (1987) Phil Phtopath 23:1–7. On farm trails of a fungus *Paecilomyces lilacinus* against potato cyst nematode and other species in Benguet province.
15. Dickson DW & Mitchell DJ (1985) J. Nematol. 17:519. Evaluation of *Paecilomyces lilacinus* as a biocontrol agent of *Meloidogyne Jvanica* on tobacco.
17. Dube B & Smart GC (1987) J. Nematol. 19:222–227. Biological control of *Meloidogyne incognita* by *Paecilomyces lilacinus* and *Pasteuria penetrans*.
18. Dunn MT, Sayre RM, Carrell A & Wergin WP (1982) Scann Electr Microscop 3:1351–1357. Colonizatioin of nematode eggs by *Paecilomyces lilacinus* (Thom) Samson as observed with scanning electron microscopy.
19. Franco J, Jatala P & Bocangel M (1981) J Nematol 13:438–439. Efficiency of *Paecilomyces lilacinus* as a biocontrol agent of *Globodera pallida*.

(List continued on next page.)

*Primary Examiner*—Irene Marx
*Attorney, Agent, or Firm*—Christie, Parker & Hale, LLP

[57] ABSTRACT

Isolates of *Paecilomyces lilacinus*, *Paecilomyces lilacinus* 251 (AGAL 89/030550), *Paecilomyces lilacinus* 252 (AGAL 90/028188A), *Paecilomyces lilacinus* 253 (AGAL 90/028188B), and *Paecilomyces lilacinus* 254 (AGAL 90/028188C), which exhibit aggressive and fast nematicidal activity at commercially useful spore concentrations and methods of using the disclosed strains of *P. lilacinus* to biologically control nematode infestation in crop plants, thereby reducing the need for chemical nematicides.

9 Claims, 4 Drawing Sheets

OTHER PUBLICATIONS

20. Fioretto AMC & Villacorta A (1989) Pesq Agropec Bras Brasilia 24:975–978. Exigencias termicas para O desenvolvimento do fungo nematogeno *Paecilomyces lilacinus*.

21. Freire FCO & Bridge J (1985) Fitopatol Bras 10:577–596. Parasitism of eggs, females and juveniles of *Meloidogyne incognita* by *Paecilomyces lilacinus* and *Veticillium chlamydosporium*.

23. Generalao LC & Davide RG (1986) Phil Phytopath. 22:36–41. Biological control of *Radopholus similis* on banana with three nematophagous fungi.

24. Hewlett TE, Dickson DW, Mitchell DJ & Kammwischer Mitchell ME (1988) J. Nematol. 20:578–584. Evaluation of *Paecilomyces lilacinus* as a biocontrol agent of *Meloidogyne javanica* on tobacco.

26. Inch JM & Trinci APJ (1987) J Gen Microbiol 133:247–252. Effects of water activity on growth and sporulation of *Paecilomyces farinosus* in liquid and solid media.

27. Jarfee BA & Muldoon AE (1989) J. Nematol. 21:50–510. Suppression of cyst nematode by natural infestation of nematophagous fungus.

30. Jatala P (1986) Ann. Rev. Phtopathol. 24:453–489. biological control of plant parasitic nematodes.

31. Jatala P, Kaltenbach R & Bocangel M (1979) J. Nematol. 11:303. biological control of *Meioidogyne incognita acrita* and *Globodera pallida* on potatoes.

32. Jatala P, Kaltenbach R, Devaux AJ & Campos R (1980) J. Nematol. 12:226–227. Field application of *Paecilomyces lilacinus* for controlling *Meloidogyne incognita* on potatoes.

33. Jatala P, Salas R, Kaltenbach R & Bocangel M (1981) J. Nematol. 13:445. Multiple application and long term effect of *Peecilomyces lilacinus* in controlling *Meloidogyne incognita* under field conditions.

34. Khan TA & Husain SI (1988) Indian J. Nematol. 18:192–198. Studies on the efficacy of seed treatments with pesticides, oilcakes, neem–leaf and culture liltrate of the *Paecilomyces illacinus* for the control of diseases caused by the presence of *Rotylenchulus reniformis, Meloidogyne incognita* and *Rhizoctonia solani* either individually or concomitantly on cowpea.

35. LaMondia JA & Brodie BB (1984) J. Nematol. 16:112–115. An observation chamber technique for evaluating potential biocontrol agents of *Globodera rostochiensis*.

40. Mitchell DJ Kannwischer–Mitchell ME & Dickson DW (1987) J. Nematol. 19:255–256. A semi–selective medium for the isolation of *Paecilomyces lilacinus* from soil.

41. Molina GC & David8 RG (1988) Phil. Agr.69:173–186. Evaluation of microbial extracts for nematicidal activity against plant parasitic nematodes *Meloidogyne incognita* and *Radopholus similis*.

42. Morgan–Jones G & Rodiquez–Kabana R (1984) Phytopathology vol? Species of Verticillium and Paecilomyces as parasites of cyst and root–knot nematodes.

48. Reddy PP & Khan RM (1989) Pak J Nematol 7:55–59. Evaluation of biocontrol agent *Paecilomyces lilacinus* and carbofuran for the management of *Rotylenchulus reniformis* infecting brinjal.

49. Rombach MC, Aguda RM, Shepard BM & Roberts DW (1986) J. Invertebr. Pathol.48:174–179. Entomopathogenic fungi (Deuteromycotina) in the control of the black bug of rice, *Scotinophara coarctata* (Hamiptera, Pentatomidae).

50. Samson RA (1974) Studies in Mycology 6:1–119. Paecilomyces and some allied hyphomycetes.

51. Sayre RM (1986) Crop Protect. 5:268–276. Pathogens For Biological Control of Nematodes.

52. Shahzad S & Ghaffar A (1987) Int. Nematol. Network Newsl. 4:33–34. Field Application Of *Paecilomyces Lilacinus* and furadan for the control of root–knot disease of okra and mung.

54. Sharma A & Trivedi PC (1989) Nematol Medit 17:131–133. Control of root–knot nematodes on *Trigonella foenum–graecum* by *Paecilomyces lilacinus*.

55. Smith OP (1986) Paper 2nd Int Workshop biol Control of Nematodes, Feb. 9–16 at PCARRD Conf Hall, Los Banos, Laguna, The Phillipines. A farmer's experience of the use of *Paecilomyces lilacinus* for the control of the potato cyst nematode *Globodera rostochiensis* in the Phillipines.

56. Tandingan IC & Davide RG (1986) Phil Phytopath 22:42–48. Biological control of *Tylenchulus semipenetrans* on citrus and *Radopholus similis* on banana with *Paecilomyces lilacinus* and *Penicillium anatolicum*.

57. Tribe HT (1980) Parasitology 81:619–639. Prospects for biological control of plant parasitic nematodes.

58. Villaneuva LM & Davide RG (1984) Phil Agr 67:223–231. Influence of pH, temperature, light and agar media on the growth and sporulation of a nematophagous fungus. *Paecilomyces lilacinus* (Thom.) Samson.

59. Villaneuva LM & Davide RG (1984) Phil Agr. 67:361–371. Evaluation of several isolates of soil fungi for biological control of root–knot nematodes.

60. Zaki FA & Bhatti DS (1988) Current Science 57=153. Economical method for mass culturing of *Paecilomyces lilacinus* (Thom) Samson.

MYCONEMATICIDES AND METHODS FOR
USING THE SAME

CROSS-REFERENCE TO RELATED APPLICATION

This is a continuation of application Ser. No. 08/400,539, filed Mar. 8, 1995 and Ser. No. 07/838,249, filed Mar. 3, 1992, now both abandoned. This application was filed under 35 USC 371 as national phase of PCT/A690700325.

FIELD OF INVENTION

The present invention relates to novel strains of *Paecilomyces lilacinus* (Thom) Samson, myconematicides containing spores of strains of *Paecilomyces lilacinus* and to methods for controlling nematode infestation.

BACKGROUND OF THE INVENTION

Damage and destruction of valuable field crops and horticultural cultivations due to infestation by plant parasitic nematodes is a serious problem to agriculture, causing considerable economic loss. In the past, control of nematodes has generally required the field application of chemical nematicides. However, chemical nematicides invariably lose their effectiveness due to nematodes developing resistance as well as build-up of soil organisms that can cause their degradation. In addition, application of chemical nematicides is often environmentally undesirable and, in recent years many have been withdrawn from the market due to their toxicity and persistence in the environment.

Biological control of nematodes would be an attractive alternative to the use of chemical nematicides and many laboratory experiments have indicated that there is good potential for the use of nematophagous fungi in such an approach. However, when experiments have been extended to non-sterile soil in a genuine cropping cycle, invariably the results have been disappointing. No doubt, as a consequence, Stirling (1988, "Biological Control of Plant Parasitic Nematodes" in "Diseases of Nematodes" Vol. II [Eds G. O. Poinar and H-B Jansson] pp 93–139, CRC Press Inc., Boca Raton, Fla.) has recently predicted that "biological control will remain an insignificant component of nematode control programmes, at least until the turn of the century". The reason usually advanced for such experimental failure is that the soil ecosystem involves a highly complex interaction between different microorganisms, and that it would be very difficult to manipulate such a system with economically feasible additions of other microorganisms (Van Gundy, 1985, In "Biological Control in Agricultural AIPM Systems"; (Eds M. A. Hoy and D. C. Herzog) pp 468–478, Academic Press.

Over 150 species of soil fungus are known to attack and destroy nematodes and extensive reviews are available in the literature (Jatala 1986, Ann. Rev. Phytopathol. 24, 459–489). Nematophagous fungi are broadly divided into two groups, (1) nematode-trapping fungi which produce mechanical or adhesive traps; and (2) endoparasitic fungi which infect nematodes when their conidia (spores) are ingested or adhere to the cuticle.

In the past there have been attempts to use nematode-trapping fungi, which are dependent on the presence of soil nematodes for growth, as biological control agents. An example of such is the commercial preparations based on Artrobotrys spp. However, these preparations have met with very limited success.

Some saprophytic soil fungi can parasitism nematode eggs (Stirling, supra). Because fungi of this type can have a dramatic effect on soil nematode populations, they are among the most interesting for their biological control (Sterling & Manakau, 1978, Mycologia 70 774–783). Jatala et al. (1979 J. Nematol. 11, 303) claimed that *Paecilomyces lilacinus* was an effective parasite of the eggs of Meloidogyne spp. and Globodera spp. A methodology was developed for the application of a Peruvian isolate of *P. lilaninus* and a large number of investigators in different countries were involved in trials with this particular organism. Whilst some results are apparently encouraging, little has been published of this work and that which has been, in many cases, is inconclusive (Jatala, 1986 Ann. Rev. Phytopathol. 24, 459–489).

A review of the literature over the last five years suggests that while there has been substantial laboratory and glasshouse experimentation on biological control of plant parasitic nematodes, the overall picture is confused and lacks consistent demonstration of any immediate practical application to agriculture. In regard to *P. lilacinus* spores obtained from mycelia grown on rice hulls and rice bran mixture, or chopped water lily and incorporated into the soil gave significant control of *Meloidogyne incognita* infesting okra (Davide & Zorilla, 1985, Phil. Agric. 68, 493–500). Good results were also found against *M. incognita* on corn, tomato and okra in glasshouse experiments in comparison with the chemical nematicide Aldicarb (Ibrahim at al., 1987, Nematol. Medit. 15, 265–268). However, inconclusive results against M. incognita were obtained when mixtures of *P. lilacinus* and *Pasteuria penetrans* were used in experiments involving *Vicia villosa* (Dube & Smart, 1987, J. Nematol. 19, 222–227). Hewlett et al. (J. Nematol. 20, 578–584, 1988) found that *P. lilacinus* did not control *Meloidogyne javanica* over a two year field experiment on tobacco and actually produced lower yields than all other treatments. In another group of experiments, Culbreath et al. (Nematotrop. 16, 153–166, 1986) tested the effects of a mixture of *P. lilacinus* and chitin for controlling *Meloidogyne arenaria*. The levels of material added, however, would prohibit any commercial application. Brazilian experiments by Novaretti et al. (Nematol. Brasil. 10, 133–144, 1986) led to substantial decreases in yield and no control of Pratylenchus spp. on sugar cane. Such inconsistent results in experiments using *P. lilacinus* indicate underlying problems in present approaches to its wide spread application as a biological control agent for nematodes. It has been suggested (Cabamilis et al., 1989, J. Nematol. 21, 164–172) that such variability in results may be caused by mutations. They go on to attribute loss of effectiveness as nematophagous agents in Peruvian isolates to culture material being kept with periodic transfer on media in the absence of nematodes.

Even in regard to some apparently successful field experiments using *Paecilomyces lilacinus*, Stirling (supra) suggests "that there is lack of convincing evidence that the introduced fungus was responsible for the observed reductions in nematode population".

To summarise existing technical knowledge, it is well established that many naturally occurring soil fungi are capable of parasitising and killing nematodes. However, use of these for biological control in realistic agricultural contexts in the past has met with mixed success and in a number of cases the form of the fungus administered to the soil is such that it would not be applicable to commercial use.

DESCRIPTION OF THE PRESENT INVENTION

The present applicants have isolated a strain of *Paecilomyces lilacinus* designated 251 from a Meloidogne egg mass in Los Baños, Philippines, which is strongly nematophagous and has demonstrated the unexpected ability to parasitise and destroy larvae, cysts and adults of the common genera of plant parasitic nematodes. A sample of this strain was deposited with the Australian Government Analytical Laboratories (AGAL) at 1 Suakin Street, Pymble, New South Wales, 2073, Australia on Aug. 2 1989 and was accorded accession No. 89/030550.

P. lilacinus is a widely distributed saprophytic soil fungus which is readily isolatable throughout the world. It is believed, however, that strains having the characteristics of the strains of the present invention have not been isolated previously.

P. lilacinus strain 251 has been shown to be effective under field conditions against plant pathogenic nematodes which attack a variety of agriculturally important crops including banana, potato, pineapple, cotton, coffee, rice, black pepper, okra, avocado, tomato etc. In vitro tests for nematicidal activity have demonstrated this strain to be effective in killing several nematode species including Meloidogyne spp. *Radopholus similis*, Pratylenchus spp., *Rotylenchus reniformis, Globodera rostochiensis, Helicotylenchus multicinctus, Tylenchulus semipenetrans,* Tylenchorhynchus spp., Hoplolaimus spp., Criconemoides spp., Hemicycliophora spp., and Xiphinema spp. This broad spectrum of nematophagous activity from a fungus which is better known as being effective against Meloidogyne eggs, prompted the present inventors to study a number of the characterisics of *Paecilomyces lilacinus* strain 251 in an attempt to identify those characteristics of *P. lilacinus* which relate to nematicidal activity.

It is believed that identification of such characteristics will enable the selection of strains of *P. lilacinus* which are strongly nematophagous and which will, therefore, have application in biological control of nematodes. The present inventors studied allozyme profiles of twenty-one enzyme activities and the temperature growth profile of twelve isolates of *Paecilomyces lilacinus* including the 251 strain and the type strain (NRRL 895). These studies enabled the separation of the twelve isolates into two groups, one group including strain 251 and three other strongly nematophagous strains (designated 252, 253 and 254), and the other group including the type strain, based on a number of characteristics. These characteristics included the inability to grow at temperatures of 33° C. and the allozyme pattern, particularly in regard to six enzymes. Of these enzymes the most useful in separating the two groups was lactate dehydrogenase$^A$ followed by, in order of decreasing usefulness, lactate dehydrogenase$^C$ asparate aminotransferase$^C$, fructose-1,6-diphosphatase, phosphoglycerate mutase and hexokinase.

Accordingly in a first aspect the present invention consists in a myconematicide comprising spores of a strain(s) of *Paecilomyces lilacinus* and a nematicidal carrier, characterised in that the strain of *P. lilacinus* has an allozyme profile identical to that of *P. lilacinus* strain 251 in respect of lactate dehydrogenase$^A$.

In a preferred embodiment of the present invention the strain(s) of *P. lilacinus* has an allozyme profile identical to that of *P. lilacinus* strain 251 in respect of lactate dehydrogenase$^A$ and lactate dehydrogenase$^C$.

In a further preferred embodiment of the present invention the strain(s) of *P. lilacinus* has an allozyme profile identical to that of *P. lilacinus* strain 251 in respect of lactate dehydrogenase$^A$, lactate dehydrogenase$^C$ and at least one enzyme selected from the group consisting of aspartate aminotransferase$^C$, fructose-1,6-diphosphatase, phosphoglycerate mutase and hexokinase.

In yet a further preferred embodiment of the present invention the strain(s) of *P. lilacinus* will not grow at a temperature greater than or equal to 33° C.

In a second aspect the present invention consists of a myconematicide comprising a nematicidal carrier and spores of a strain(s) of *P. lilacinus*, the strain being selected from the group consisting of strain 251, strain 252, strain 253, strain 254 and combinations thereof.

In a preferred embodiment of this aspect of the present invention the spores are *P. lilacinus* strain 251.

In a further preferred embodiment of this aspect of the present invention the spores are present at a concentration of between about $1\times10^5$ and about $1\times10^{10}$ spores/gram of carrier, and more preferably at a concentration of between about $5\times10^7$ and about $5\times10^9$ spores/gram of carrier.

The myconematicide may be formulated as a powder or in a pelleted form. In this case, it is preferred that the carrier is formulated so that slow release of the spores is obtained over a considerable period of time following application of the myconematicide.

The *P. lilacinus* strains may be cultured and caused to sporulate using methods well known in the art. Harvesting of spores is preferably performed under conditions that do not promote heat, including shaking, scraping, washing and centrifugation. The spore material is then dried by a suitable process such as air drying, freeze drying or desiccation with a suitable desiccant and can be reformulated by addition of inert filler or new growth material to provide a suitable number of spores per unit amount of product.

*P. lilacinus* strain 251 has been successfully field trialed for a period of six years at different levels of inoculation and application methods on a wide variety of ornamental and crop plants with no diminution of its nematicidal properties. The genetic stability of this strain can be maintained through standard procedures well-known in the art. These typically involve testing, storage by desiccation on silica gell or freeze drying and ensuring minimal passaging of the strain.

The composition may be formulated in accordance with a variety of known preparations, in particular for use in coating seeds. A variety of polysaccharides or crude plant products such as cornmeal may be used as fillers to assist fungal growth. Likewise, whole seeds such as wheat or sesame may be used to present the fungus. Mineral matter, such as silica and vermiculite may also be added. The material is then packed preferably under essentially anaerobic conditions.

In further aspects the present invention consists in substantially pure cultures of *P. lilacinus* strain 251, *P. lilacinus* strain 252, *P. lilacinus* strain 253 and *P. lilacinus* strain 254.

As stated above, a sample of *P. lilacinus* strain 251 was deposited with the Australian Government Analytical Laboratories (AGAL) at 1 Suakin Street, Pymble, New South Wales, 2073, Australia, on Aug. 2, 1989 and was accorded Accession No. 89/030550. In addition, samples of strains 252, 253 and 254 were also lodged with this Depository on Jul. 31, 1990 and accorded Accession Nos. 90/028188A, 90/028188B, 90/028188C respectively.

In a further aspect the present invention consists in a method for the control of nematode infection in a crop comprising applying an effective amount of infective propagules of strain(s) of *P. lilacinus*, the strain(s) having an allozyme profile identical to that of *P. lilacinus* strain 251 in respect of lactate dehydrogenase$^A$.

In a preferred embodiment of this aspect of the present invention the strain of *P. lilacinus* has an allozyme profile identical to that of *P. lilacinus* strain 251 in respect of lactate dehydrogenase$^A$ and lactate dehydrogenase$^C$.

In a further preferred embodiment of this aspect of the present invention the strain of *P. lilacinus* has an allozyme profile identical to that of *P. lilacinus* strain 251 in respect of lactate dehydrogenase$^A$ lactate dehydrogenase$^C$ and at least one enzyme selected from the group consisting of aspartate aminotransferase$^C$, fructose-1,6-diphosphatase, phosphoglycerate mutase and hexokinase.

In yet a further preferred embodiment of this aspect of the present invention the strain(s) of *P. lilacinus* will not grow at a temperature greater than or equal to 33° C.

In yet a further preferred embodiment of this aspect of the present invention the strain of *P. lilicanus* is selected from the group consisting of strain 251, strain 252, strain 253 and strain 254, and is most preferably strain 251.

As used herein, the term "effective amount" is defined as an amount sufficient to display the nematicidal activity.

The infective propagules of the *P. lillacinus* strain may be applied to the crop either in a liquid suspension, in association with a suitable nematicidal carrier, or as a solid formulation, in association with a suitable excipient.

At present it is preferred that the dosage of infective propagules of the *P. lilacinus* strain is in the order of about $1 \times 10^7$ spores per gram of soil for nursery applications and for field applications between $1 \times 10^7$ and $1 \times 10^8$ spores per ml of an aqueous suspension which is then applied as a drench to soil adjacent to plants. In the case of banana this dosage translates to about 150 ml of aqueous drench per mat.

The myconematicide of the present invention may be applied to crops using any of the methods well known in the prior art. In a number of cases it is advantageous if the myconematicidal composition is provided in the environment of the roots so minimizing the root damage caused by nematodes. This may be achieved by coating of seeds with the composition so that emergence of roots results in a fungal inoculum in their environment; by dipping, or spraying the root regions of seedlings or seed trays in a nursery situation; or application of the composition at the site of planting, either in aqueous suspension or in solid form. This may, of course, be done in conjunction with treatment with appropriate agricultural material such as fertilizer. It is particularly preferred that the nematicidal composition of the present invention is specifically applied to the regions of the plant rhizosphere affected by nematodes. For example, an injection device can be used to apply the nematicidal composition as an aqueous suspension adjacent to the corm of banana infested by Radopholus spp.

The plants to which the nematicidal composition of the present invention may be administered are typically agriculturally significant crop plants but also include ornamental plants. Control of plant parasitic nematodes by the myconematicidal composition has been found in a wide variety of plants, including banana, sugar cane, pineapple, okra, coffee, cacao, black pepper, tobacco, ramie, cotton, rice, wheat, barley, oat, corn, citrus, grape, tomato, potato, carrot, pea, bean, various horticultural crops and a variety of tropical fruits including papaya and avocado. As the fungus is generally not persistent for a long period of time in the complex soil ecosystem, it is presently preferred that with perennial crops such as banana that the nematicidal composition is reapplied at least every six months.

It is also believed that *P. lilacinus* strain 251 may be useful in the control of parasitic nematodes which infest domestic animals. In order to use the novel strains of the present invention in such an application it is believed to be necessary to coat the propagules in such a way that they are protected during passage through the animal's alimentary tract and released in the faeces. Such protection may be obtained by embedding the fungal material in a matrix which is insoluble in the gastrointestinal environment. This matrix material may be selected from a wide variety of natural and synthetic substances such as waxes, resins, polysaccharides, starches, mineral matter or vegetable matter.

Laboratory tests, as well as field observations made on treated potato crops, indicate that *P. lilacinus* strain 251 also controls tuber and root rotting fungi such as *Sclerotium rolfsii* and *Rhizoctonia solani*. It has also been observed that as nematode infestation decreases, inevitably the incidence of bacterial wilt diminishes.

BRIEF DESCRIPTION OF THE DRAWINGS

In order that the nature of the present invention may be more clearly understood, preferred forms thereof will now be described with reference to the following accompanying drawings in which.

EXAMPLE 1

Figure 1:
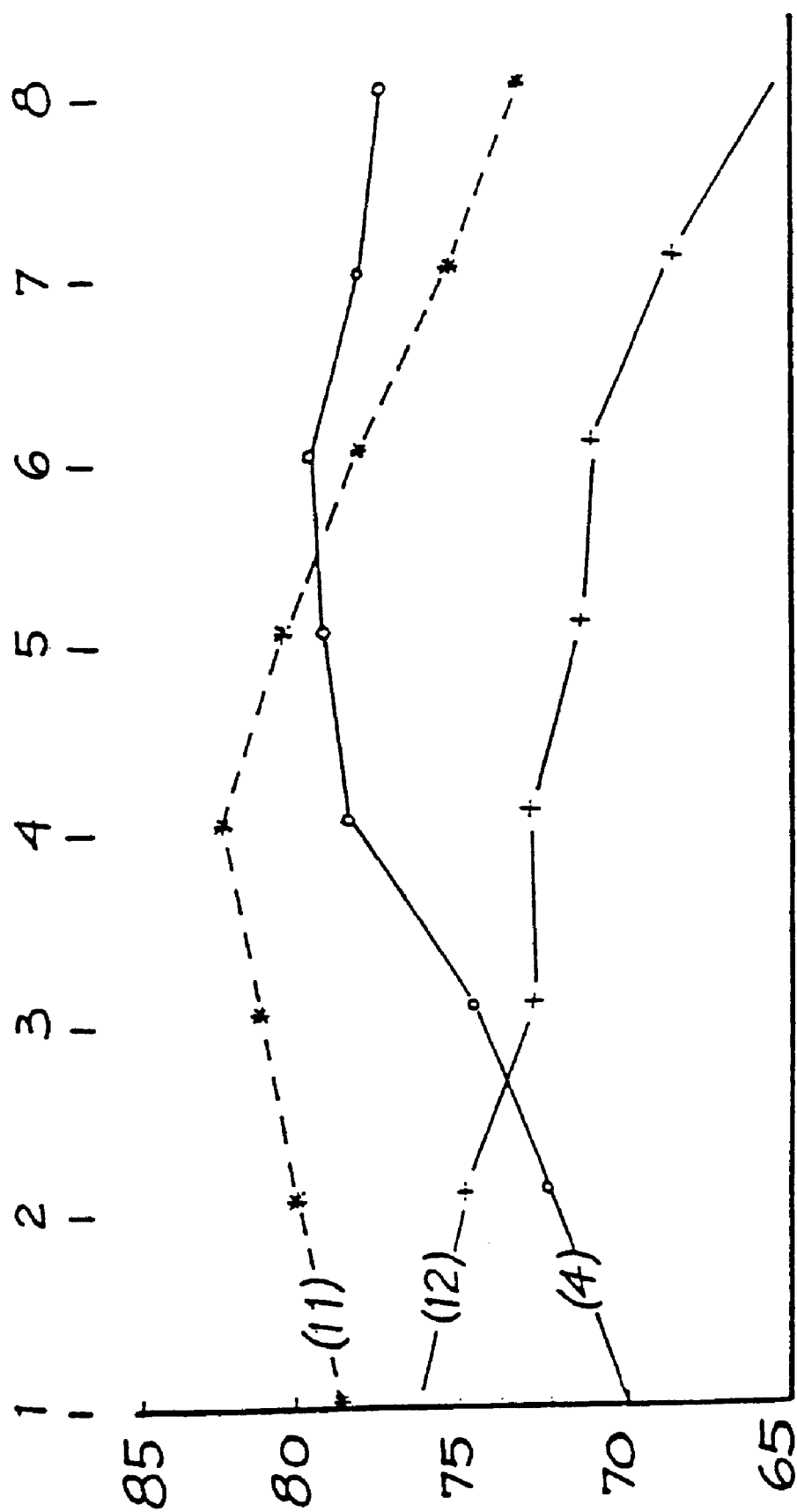
FIG. 1. Changes in proportional function root volume at three month intervals in a field experiment on banana starting June, 1987. (4)—myconematicide with between $1 \times 10^9$ and $1 \times 10^{10}$ infective propagules applied to each banana mat at six month intervals (11)—Furadan applied to each banana mat at six month intervals. Nematicides first applied June, 1987. (12)—untreated control.

Parasitism in vitro of Various Nematodes by *P. lilacinus* Strain 251

*P. lilacinus* is generally regarded as oviparsitic to nematode egg masses. This example demonstrates that the 251 strain is also endoparasitic to various growth stages of common plant parasitic nematode genera. Spores were produced by solid phase fermentation using rice hulls as described above and added at a concentrations of $1 \times 10^5$/ml to petri dishes containing populations of larvae and adults of various species of plant-parasitic nematodes isolated from roots of a variety of infested plants. After inoculation, the spores were allowed to incubate for 48 hours at room temperature. The results of the series of experiments are summarized in Table 1.

These results show that the fungus is capable of attacking and killing nematodes that are both endoparasitic and semi-endoparasitic. The results indicate effectiveness at different developmental stages against nematodes with a variety of life styles. The fungus parasitizes by means of its spores, that either adhere to the cuticle or enter the body of the nematode host through the stoma, anus or the opening of the reproductive organ. The germ tube of a spore adhering to the cuticle actually penetrates the body wall as a spore germinates and grows. Three days after inoculation a high level of mortality was observed among eleven different nematode genera examined. After five days in six of the eleven genera examined more than 80% of individuals were killed. Such experiments clearly demonstrate the ability of strain 251 to parasitize and kill larval and adult plant-parasitic nematodes.

of laboratory and field tests. Details of these strains are summarized in Table 2.

The results of the allozyme study are summarized in Table 4. As can be seen, whilst the twelve strains are related, the allozyme profiles allowed significant differentiation to be made between two groups nematophagous and otherwise.

TABLE 1

PERCENTAGE MORTALITY OF DIFFERENT PLANT PARASITIC NEMATODES AFTER INOCULATION OF *P. lilacinus* strain 251 AT 100,000

SPORE CONCENTRATION
% MORTALITY

| Nematode species | 2 DAYS | 3 DAYS | 4 DAYS | 5 DAYS | 6 DAYS | 7 DAYS | 8 DAYS | 9 DAYS | 10 DAYS | 11 DAYS |
|---|---|---|---|---|---|---|---|---|---|---|
| ENDOPARASITIC | | | | | | | | | | |
| *Radopholus similis* | 52.5 | 75 | 80 | 100 | — | — | — | — | — | — |
| *Meloidogyne* spp. 2nd stage larva | 35 | 45 | 55 | 60 | 80 | 80 | 80 | 80 | 80 | 80 |
| *Pratylenchus* spp. female | 22.5 | 45 | 57.5 | 65 | 77.5 | 87.5 | 87.5 | 95 | 95 | — |
| *Rotylenchulus reniformis* 4th stage larva | 50 | 70 | 87.5 | 90 | 95 | 100 | — | — | — | — |
| *Globodera rostochiensis* female | 42.5 | 50 | 75 | 100 | | | | | | — |
| *Helicotylenchus multicinctus* | 37.5 | 60 | 80 | 90 | 95 | 95 | 95 | 95 | — | — |
| *Tylenchulus semipenetrans* larva | 45 | 60 | 70 | 80 | 90 | 90 | 90 | 90 | 90 | — |
| *Tylenchorhynchus* spp. | 22.5 | 40 | 52.5 | 60 | 67.5 | 80 | 82.5 | 82.5 | 82.5 | — |
| *Hoplolaimus* spp. | 22.5 | 40 | 42.5 | 50 | 57.5 | 77.5 | 82.5 | 87.5 | 87.5 | — |
| *Criconemoides* spp. | 12.5 | 42.5 | 50 | 57.5 | 87.5 | 90 | 97.5 | 97.5 | 100 | — |
| *Hemicycliophora* spp. | 17.5 | 30 | 35 | 40 | 55 | 57.5 | 60 | 60 | 60 | — |
| *Xiphinema* spp. | 47.5 | 65 | 82.5 | 92.5 | 100 | — | — | — | — | — |

EXAMPLE 2

Allozyme Studies

Complete allozyme electrophoresis profiles were prepared for twenty-one enzymic activities on the twelve isolates of *P. lilacinus* set out in Table 2. The eighteen enzymes studied are set out in Table 3. These fungal isolates listed in Table 2 were maintained on potato dextrose agar (Oxoid) at 21° C. Spores were transferred to fresh plates at approximately fortnightly intervals. The cultures were maintained desiccated on silica gel.

The allozyme experiments were performed under standard conditions used for allozyme typing of many organisms, according to the methods set out in "Allozyme Electrophoresis: A Handbook for Animal Systematics and Population Studies" B. J. Richardson, P. R. Baverstock and M. Adams (Academic Press, Sydney, 1986, 410 pages). Fungal mycelia were removed from *P. lilacinus* cultures growing on potato dextrose agar, frozen at −80° C. and macerated on thawing. Aliquots of material were loaded on Cellogel (Chemetron, Milan) gels. Eight strains of *P. lilacinus* designated by AFRR prefix were obtained from the culture collection of Dr. A. Hocking (CSIRO Division of Food Processing). In addition to the type strain, this collection included isolates from soil in Australia, Papua New Guinea and U.S.A. In addition two Australian isolates of animal origin were included; these were one strain isolated from the human cornea and another from a crocodile which died in the Melbourne Zoo. A further four isolates from the Philippines, including *P. lilaninus* strain 251 (AGAL, 89/030550) were included. These four strains were selected as effective nematophagous strains on the basis of a variety

TABLE 2

PAECILOMYCES LILACINUS ISOLATES

| | | |
|---|---|---|
| 1. FRR 1185 | acetocarmine soln, USA. G. Ledingham, 1940 |
| 2. FRR 3427 | pandanus nuts, PNG Sthn Highlands, A. Hocking, 1984 |
| 3. 252 | Philippine nematicidal strain, accessed 1989 |
| 4. 251 | Philippine nematicidal strain, accessed 1989 |
| 5. FRR 2410 | human cornea, Sydney Hospital, F. Jennis, 1981 |
| 6. FRR 3430 | pandanus nuts, PNG Central Province, A. Hocking, 1984 |
| 7. 253 | Philippine nematicidal strain, accessed 1989 |
| 8. 254 | Philippine nematicidal strain, accessed 1989 |
| 9. FRR 3587 | coral cay soil, Great Barrier Reef. Rcd from J. Walker, 1988 |
| 10. FRR 338 | soil, MIA, NSW. J. PItt, 1970 |
| 11. FRR 3319 | crocodile hatchling, Melbourne Zoo. M. Maslen, 1986 |
| 12. FRR 895 | TYPE Strain Edgerton, 1908. Rcd from NRRL, 1969 |

TABLE 3

| ENZYMES | ABBREVIATION | E. C. NUMBER |
|---|---|---|
| Aspartate Aminotransferase | AAT | 2.6.1.1 |
| Enolase | ENOL | 4.2.1.11 |
| Aldolase | ALDOL | 4.1.2.13 |
| Phosphoglucomutase | PGM | 2.7.5.1 |
| Phosphoglycerate Mutase | PGAM | 2.7.5.3 |
| Malate Dehydrogenase | MDH | 1.1.1.37 |
| Fumarate Hydratase | FUM | 4.2.1.2 |
| Adenosine Deaminase | ADA | 3.5.4.4 |
| Pyruvate Kinase | PK | 2.7.1.40 |
| Fructose-1,6-Diphosphate | FDP | 3.1.3.11 |
| Malic Enzyme | ME | 1.1.1.40 |

TABLE 3-continued

| ENZYMES | ABBREVIATION | E. C. NUMBER |
|---|---|---|
| Glutamate-Pyruvate Transaminase | GPT | 2.6.1.2 |
| Lactate Dehydrogenase | LDH | 1.1.1.27 |
| Hexokinase | HK | 2.7.1.1 |
| Superoxide Dismutase | SOD | 1.15.1.1 |
| Glucose-Phosphate Isomerase | PGI | 5.3.1.9 |
| Phosphoglycerate Kinase | PGK | 2.7.2.3 |
| Aconitrate Hydratase | ACON | 4.2.1.3 | the basis of their maximum growth temperature. The four isolates known to be nematophagous on plant parasitic nematodes, namely strains 251, 252, 253 and 254, did not grow above 33° C. This would tend to suggest that these strains are extremely unlikely to be able to cause systematic mycosis in mammals.

The remaining eight strains were all capable of growing at 33° C. but their growth was slower than that at the optimum temperature (25–30° C.). None of the twelve strains examined were capable of growth at 37° C. All strains had similar growth profiles at the low end of the growth curve and in terms of the optimal growth temperature. Growth was essentially absent in all twelve strains at

TABLE 4

ELECTROPHORETIC MOBILITIES FOR 21 ENZYMES OF P. LILACINUS

| | STRAIN | $AAT^C$ | ENOL | ALDOL | PGM | PGAM | MDH | $FUM^C$ | ADA | PK | FDP | ME |
|---|---|---|---|---|---|---|---|---|---|---|---|---|
| 1 | FRR 1185 | 3 | 1 | 2 | 1 | 4 | 2 | 2 | 1 | 2 | 3 | 2 |
| 2 | FRR 3427 | 3 | 1 | 2 | 1 | 2 | 2 | 2 | 1 | 2 | 5 | 2 |
| 3 | 252 | 2 | 1 | 2 | 1 | 2 | 2 | 2 | 1 | 2 | 3 | 2 |
| 4 | 251 | 2 | 1 | 2 | 1 | 2 | 2 | 2 | 1 | 2 | 3 | 2 |
| 5 | FRR 2410 | 3 | 1 | 2 | 1 | 2 | 2 | 2 | 1 | 2 | 3 | 2 |
| 6 | FRR 3430 | 3 | 1 | 2 | 1 | 2 | 2 | 2 | 1 | 2 | 5 | 2 |
| 7 | 253 | 2 | 1 | 2 | 1 | 2 | 2 | 2 | 1 | 2 | 3 | 2 |
| 8 | 254 | 2 | 1 | 2 | 1 | 2 | 2 | 2 | 1 | 2 | 3 | 2 |
| 9 | FRR 3587 | 2 | 1 | 2 | 1 | 2 | 2 | 2 | 1 | 2 | 4 | 2 |
| 10 | FRR 338 | 3 | 1 | 2 | 1 | 4 | 2 | 2 | 1 | 2 | 2 | 2 |
| 11 | FRR 3319 | 2 | 1 | 2 | 1 | 4 | 2 | 2 | 1 | 2 | 6 | 2 |
| 12 | FRR 895 | 3 | 1 | 2 | 1 | 4 | 2 | 2 | 1 | 2 | 3 | 2 |

| | STRAIN | GPT | $LDH^A$ | $LDH^C$ | HK | SOD | $AAT^A$ | PGI | $FUM^B$ | PGK |
|---|---|---|---|---|---|---|---|---|---|---|
| 1 | FRR 1185 | 2 | 2 | 3 | 1 | 1 | 1 | 1 | 1 | 1 |
| 2 | FRR 3427 | 2 | 2 | 3 | 1 | 1 | 1 | 1 | 1 | 1 |
| 3 | 252 | 2 | 1 | 2 | 1 | 1 | 1 | 1 | 1 | 1 |
| 4 | 251 | 2 | 1 | 2 | 1 | 1 | 1 | 1 | 1 | 1 |
| 5 | FRR 2410 | 2 | 2 | 2 | 1 | 1 | 1 | 1 | 1 | 1 |
| 6 | FRR 3430 | 2 | 2 | 3 | 1 | 1 | 1 | 1 | 1 | 1 |
| 7 | 253 | 2 | 1 | 2 | 1 | 1 | 1 | 1 | 1 | 1 |
| 8 | 254 | 2 | 1 | 2 | 1 | 1 | 1 | 1 | 1 | 1 |
| 9 | FRR 3587 | 2 | 2 | 2 | 1 | 1 | 1 | 1 | 1 | 1 |
| 10 | FRR 338 | 2 | 2 | 3 | 1 | 1 | 1 | 1 | 1 | 1 |
| 11 | FRR 3319 | 2 | 2 | 3 | 2 | 1 | 1 | 1 | 1 | 1 |
| 12 | FRR 895 | 2 | 2 | 4 | 1 | 1 | 1 | 1 | 1 | 1 |

(Superscript "A" refers to the most anodally migrating protein in each strain while superscript "C" refers to the slower migrating protein. The numbers refer to the relative speed of migration towards the anode - 1 slowest; 6 fastest).

Although the two groups were identical in respect of fifteen enzyme activities, the remaining six enzyme activities, namely lactate dehydrogenase$^A$, lactate dehydrogenase$^C$, aspartate aminotransferase$^C$, fructose-1,6-diphosphatase, phosphoglycerate mutase and hexokinase showed considerable diversity. However, the isolates characterised as being nematophagous on plant parasitic nematodes, namely strains 251, 252, 253 and 254, were identical on the basis of all twenty-one enzyme activities studied.

The most useful enzyme in separating the two groups was seen to be lactate dehydrogenase$^A$ followed by, in order of decreasing importance, lactate dehydrogenase$^C$ aspartate aminotransferase$^C$, fructose-1,6-diphosphatase, phosphoglycerate mutase and hexokinase.

EXAMPLE 3
Growth Temperature Profiles

The growth temperature profiles of the twelve strains of P. lilacinus set out in Table 2 were examined to determine whether the isolates differed in their growth temperature profiles. The twelve isolates fell into two distinct groups on 15° C., at 21° C. growth was approximately 50% that of the optimal temperature of 25–30° C. The results of these experiments are summarized in Table 5.

TABLE 5

Growth of Strains of P. lilacinus at Different Temperatures

| P. lilacinus Strain | 15° C. | 21° C. | 33° C. | 37° C. |
|---|---|---|---|---|
| FRR1185 | − | + | + | − |
| FRR3427 | − | + | + | − |
| 252 | − | + | − | − |
| 251 | − | + | − | − |
| FRR2410 | − | + | + | − |
| FRR3420 | − | + | + | − |
| 253 | − | + | − | − |
| 254 | − | + | − | − |
| FRR3587 | − | + | + | − |
| FRR338 | − | + | + | − |
| FRR3319 | − | + | + | − |
| FRR895 | − | + | + | − |

EXAMPLE 4

Nematicidal activity of four different nematophagous strains of *P. lilacinus* united by common allozyme pattern, in comparison with a chemical nematicide.

Replicated pot tests were undertaken to examine the relative nematicidal character of different nematophagous strains of *P. lilacinus* in comparison with a widely used chemical nematicide. The amount of root-galling on tomato seedlings var. VCll-1 was used as a measure of nematode control. The results of this greenhouse experiment are shown in Table 6.

TABLE 6

Effects of Different Nematophagous Strains of *P. lilacinus* on the Control of Root-Knot Nematode (*M. incognita*) Compared with the Nematicide NEMACUR ® (Fenamiphos) 10G manufactured by BAYER. A Greenhouse Experiment using tomato seedlings Var. VC11-1 as test plants.

| Treatment | Mean Gall Index* | Mean No. Galls/plant | % Control |
|---|---|---|---|
| Strain 251 | 2.0 | 12.8 | 93.0 |
| Strain 252 | 3.8 | 90.8 | 50.4 |
| Strain 253 | 2.2 | 13.8 | 92.4 |
| Strain 254 | 2.5 | 25.0 | 86.3 |
| NEMACUR ® 10G (1 Kg. a.i./ha.) | 2.0 | 15.2 | 91.6 |
| Untreated | 5.0 | 183.0 | — |

*Gall index:
1 = No gall;
2 = trace;
3 = slight;
4 = moderate;
5 = severe galling Wherein the mean Gall Index is the arithmetic mean of the Gall Index for six replicate plants in each treatment.

The results of this experiment suggest that, although all strains tested are strongly nematicidal, strain 251 is the most effective. The experiment suggests that strains 251 and 253 are particularly effective.

EXAMPLE 5

In order to further investigate whether strain 251 should also be the preferred strain for control of Globodera open field trials on potato (var. Isola) were undertaken on a farm with soil infested with the cyst nematode. Replicated plots were individually treated with the myconematicidal composition in which the active propagules were respectively spores of the nematicidal strains 251, 253, 254 (Tubers dipped in an aqueous suspension of $1 \times 10^9$ spores/ml and subsequently planted under normal agronomic conditions). Beside the untreated control plots, the experiment also included treatment plots to which the chemical FURADAN® (Carbofuran) 3G (FMC Corporation) was applied.

The results of this experiment are shown in Table 7.

TABLE 7

Effects of Different Treatments on Potato Yields Expressed by Kg/10 m², Cyst Nematode Infected Soil, Atok, Benguet. Comparative Results of Using different Nematophagous Strains of *P. lilacinus*

| Treatments | Replicates | | | | | Standard Error |
|---|---|---|---|---|---|---|
| | I | II | III | IV | Mean | |
| Strain 251 | 15.8 | 20.7 | 16.5 | 15.0 | 17.0 | 2.542 |
| Strain 253 | 15.3 | 15.0 | 15.8 | 15.3 | 15.4 | 0.332 |
| Strain 254 | 14.2 | 14.8 | 17.7 | 15.3 | 15.5 | 1.534 |
| FURADAN ® 3G (4.5 Kg a.i/ha) | 15.0 | 16.5 | 16.7 | 16.3 | 16.1 | 0.768 |
| Untreated | 10.7 | 8.5 | 10.2 | 12.3 | 10.4 | 1.565 |

It will be seen that strain 251 performs somewhat better than the other treatments although the difference in mean yield is not significant. The improvement in yield of treated over the untreated plots is obvious and significant.

EXAMPLE 6

Nematicidal Activity of *P. lilacinus* Strain 251 in Soil

Tests were conducted to show that *P. lilacinus* strain 251 was nematicidal in different field conditions. The results of these experiments are shown in Tables 8, 9 and 10 with the tests being conducted as stated in these Tables.

Table 8 refers to an experiment on cotton at Bauang, La Union, Luzon where the dominant infesting nematodes were Rotylenchus spp. (reniform nematode) and Pratylenchus spp. (root lesion nematode). Treatments 1–3 were aqueous drenches of the myconematicidal composition containing between $1 \times 10^8$ and $1 \times 10^9$ spores of strain 251 per square meter, and treatments 4–6 were the application of the myconematicidal composition as pellets containing the same number of 251 spores as treatments 1–3. It is noted that in this experiment all levels of drench application gave similar results and provided better nematode control than did the pellet composition.

Table 9 shows the effect of the application of the myconematicidal composition containing *P. lilacinus* strain 251 spores on reducing a nematode population (Rotylenchus spp., Pratylenchus spp., Helicotylenchus spp. and Tylenchus spp.) infesting pineapple cultivated at Silang, Cavite. These results are based on replicated nematode counts carried out on 400 gms of composite soil from all the treatment replicates. Treatments 1–3 were aqueous suspensions providing levels of spores from $1 \times 10^7$ to $1 \times 10^8$ per pineapple plant rhizosphere.

TABLE 8

Pecentate decline in total plant parasitic nematodes from October 1987 to December 1987 after treatment with the strain 251 myconematicidal composition, based on replicated soil nematode counts and expressed as percentages of pretreatment numbers. Cotton, Bauang, La Union, Luzon.

| Treatments | |
|---|---|
| 1 | 24.0% |
| 2 | 25.0% |
| 3 | 25.8% |

TABLE 8-continued

Pecentate decline in total plant parasitic nematodes from
October 1987 to December 1987 after treatment with the
strain 251 myconematicidal composition, based on
replicated soil nematode counts and expressed as
percentages of pretreatment numbers. Cotton, Bauang, La
Union, Luzon.

| Treatments | |
| --- | --- |
| 4 | 34.2% |
| 5 | 37.4% |
| 6 | 38.0% |
| Control | 94.5% |

Treatments 1–3: drench equivalent to between $1 \times 10^8$ and $1 \times 10^9$ per sq. meter; 4–6 granules with same numbers of infective propagules. Wherein the nematode numbers are expressed as a percentage of pretreatment numbers.

TABLE 9

Decline in total plant parasitic nematodes after
application of strain 251 myconematicide from August, 1987
to January 1988 based on replicated soil nematode counts
and expressed as percentages of pretreatment numbers.
Pineapple, Silang, Cavite, Luzon.

| Treatment | October 1987 | December 1987 | January 1988 |
| --- | --- | --- | --- |
| 1 | 28.6% | 41.8% | 50.1% |
| 2 | 29.1% | 42.9% | 50.8% |
| 3 | 28.2% | 45.4% | 41.2% |
| Control | 115.0% | 118.0% | 91.6% |

Treatments - 1–3: drenches equivalent to between $1 \times 10^7$ and $1 \times 10^8$ propagules per plant. Wherein the nematode numbers are expressed as a percentage of pretreatment numbers.

Table 10 shows the result of the application of the myconematicidal preparation containing *P. lilacinus* strain 251 spores on the plant parasitic nematode population within the rhizosphere of ramie, cultivated at Bankal, Davao City, Mindanao. Table 10 shows percentage reduction on the total plant parasitic nematode population over a four month period as well as the percentage reduction in Maloidogyne spp. over the same period. Treatments 1–3 were aqueous suspensions providing individual plant rhizospheres from $1 \times 10^7$ to $1 \times 10^8$ spores.

TABLE 10

Decline in total plant parasitic nematodes together with
*Meloidogyne* spp. after treatment with strain 251
myconematicide from September, 1977 to January, 1988,
based on replicated nematode counts and expressed as
percentages of pretreatment numbers. Ramie, Bonkal, Davao
City, Philippines.

| | November 1987 | | January 1988 | |
| --- | --- | --- | --- | --- |
| Treatment | Total | *Meloidogyne* spp. | Total | *Meloidogyne* spp. |
| 1 | 41.6% | 56.1% | 29.2% | 70.0% |
| 2 | 50.8% | 58.6% | 35.7% | 65.3% |
| 3 | 49.4% | 52.7% | 27.7% | 74.2% |
| Control | 128.7% | 123.3% | 118.3% | 119.7% |

Treatments - 1–3: drenches equivalent to between $1 \times 10^7$ and $1 \times 10^8$ propagules per plant. Wherein the nematode numbers are expressed as a percentage of pretreatment numbers.

EXAMPLES 7 AND 8

In order to demonstrate the efficacy of the myconematicidal composition containing *P. lilacinus* strain 251 spores in controlling nematodes found infesting perennial crops, open field experiments on banana were conducted. These experiments showed improving proportional functional root volume and increasing mean bunch weight over time, thereby evidencing the efficacy of the treatment.

Figure 2:
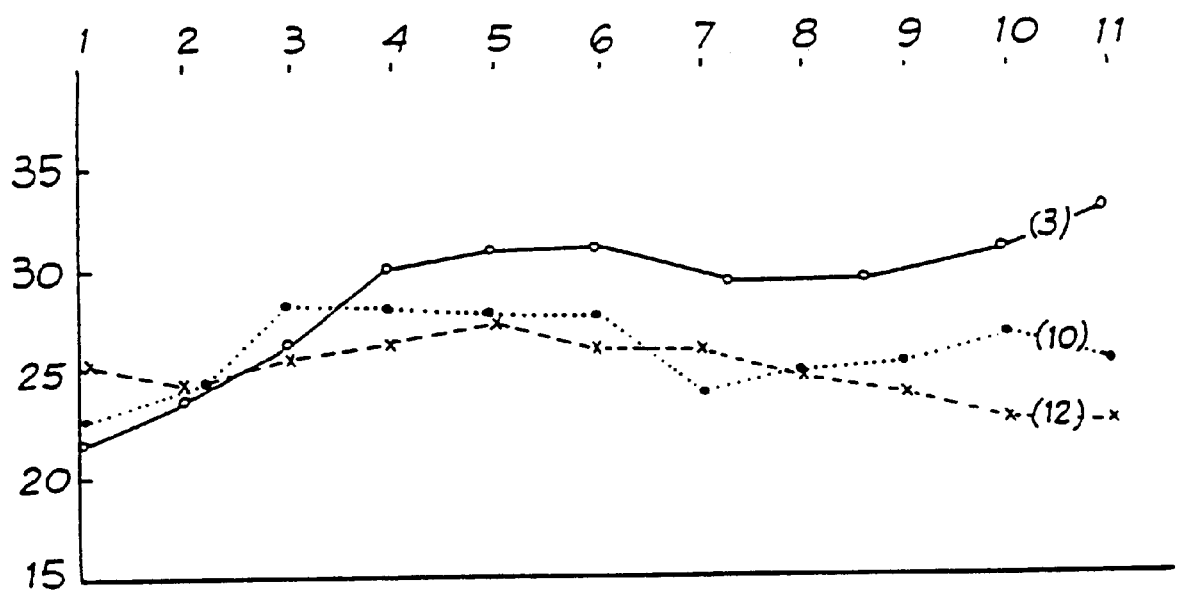
FIG. 2. Changes in average bunch weight (kg.) over two month intervals in a field experiment on banana, starting June–July 1977. (3)—myconematicide with between $1 \times 10^9$ and $1 \times 10^{10}$ infective propagules applied to each banana mat at six month intervals. (10)—NEMACUR® (Fenamiphos) applied to each banana mat at six month intervals. Nematicides first applied June, 1987. (12)—untreated control.

Results illustrated in FIGS. 1 and 2 summarise portion of a major experiment conducted at Marsman Banana Plantation, Santo Tomas, Davao del Norte, Mindanao. The experimental area was 0.6 ha of an established irrigated portion of the plantation where Giant Cavendish (Hijo) banana is cultivated. Experimental design involved five replicated blocks, each with 12 randomized treatment plots, i.e. approximately 100 banana mats were involved in each treatment. Measurements were not made on banana mats bordering treatment plots. Nine of the treatments were different types and propagule levels of myconematicides; treatments 10 and 11 shown in FIGS. 1 and 2 were chemical nematicides, respectively marketed under the names NEMACUR® (Fenamiphos, BAYER) and FURADAN® (Carbofuran, FMC Corporation). Treatment 12 was the control without nematicide treatment. Apart from nematicides, the experimental blocks received all normal inputs, including fungicides. All experimental data were collected by Marsman research staff according to standard plantation practice; chemical nematicides were applied by plantation staff according to recommended practice. The experiment was initiated in June 1987 and results are shown to April 1989 in the Figures. In accordance with plantation practice the various nematicides were applied to the treatment plots at the start of the experiment and thereafter at six-monthly intervals.

FIG. 1 depicts changes in functional root volume for three different treatments during the course of the experiment. Measurements involved standard trenching of a number of banana mats at a time near formation of the banana flower heart, taking a cubic foot of soil, and sieving the banana roots. The roots are classified into categories: dead; diseased; healthy. The data are expressed as proportional functional root volumes i.e. functional roots (=healthy plus diseased) expressed as proportion of total roots. Functional root measurements were taken from each treatment plot at approximately three month intervals during the course of the experiment. The figure shows (1) the continuous decline in the untreated control; (2) the initial improvement and then decline of Furadan; (3) the strong improvement with treatment 4, the myconematicidal composition. Functional root volume is taken as a measure of nematode activity. In this plantation, damage of the banana root is caused mainly by the nematodes Radopholus spp., Helicotyenchus spp. and Meloidogyne spp. The very good response for treatment 4, the myconematicidal composition, in part leads to the claim that the myconematicidal material is especially effective in rehabilitating badly infested crops.

FIG. 2 shows production data for three treatments presented as mean bunch weight in kilograms for two month periods over the duration of the experiment beginning with June–July 1987 and ending with March–April 1989. Treatment 10 is the chemical nematicide NEMACUR® (Fenamiphos, BAYER) and 12 is the untreated control. Treatment 3 is the myconematicidal composition produced as described wherein with growth of *P. lilacinus* strain 251 on rice hulls. The material was packaged and transported to the plantation where it was mixed as an aqueous suspension with between $1 \times 10^7$ and $1 \times 10^8$ spores per ml. The suspension was applied by pouring 150 ml. of this aqueous carrier around the daughter sucker of the banana plant. With the myconematicidal treatment mentioned in Example 7 the same procedures were adopted.

EXAMPLES 9 AND 10

In order to demonstrate the efficacy of the myconematicidal composition containing *P. lilacinus* strain 251 in controlling nematodes found infesting annual crops, open field experiments on potato were conducted. These experiments showed diminution in the nematode populations and increased yield.

Example 9 (results summarized in Tables 11 and 12) is a replicated experiment involving potato variety Isola cultivated in soil infested with the potato cyst nematode Globodera spp. at Baguias, Luzon, The Philippines. The myconematicidal preparation was applied in two ways at planting. Firstly, it was mixed in powdered form with chicken manure to give a spore concentration of between $1\times10^7$ and $1\times10^8$ per hill on planting. Second, tubers were dipped in an aqueous spore suspension of $1\times10^8$ spores/ml and subsequently planted under normal agronomic conditions. Beside the untreated control, the experiment also gives the results of treatment with the chemical nematicide FURADAN® (Carbofuran, FMC Corporation) applied according to the manufacturer's directions. Replicated soil nematode counts were made on a composite 500 gr sample taken from each of the treatment plots at the time of planting and four and twelve weeks into the experiment. The experiment reveals increase in production of more than 50% and effective control of the potato cyst nematode by the myconematicidal composition.

Example 10 (results summarized in Tables 13 and 14) shows the results of a similar experiment also with potato variety Isola and cultivated in soil infested with the root lesion nematode Pratylenchus spp. The treatments are as in Example 9. Treatment effects are very similar to those for Example 9 but here control of Pratylenchus spp. is demonstrated with an increase in production of over 70%. A similar experiment with potato variety Granola in soil infested with Pratylenchus spp. showed reduction in the nematode population to 30% of pre-treatment levels after 3 months and an increase in production of 80% over the untreated control plots.

TABLE 11

Effects of different treatments on potato yields expressed as kg/10 m², potato variety Isola. Madaymen, Baguias, Philippines, February to June, 1985. Soil infested with *Globodera* spp.

| Treatment | Replicates | | | | Mean | Standard Error |
| | I | II | III | IV | | |
|---|---|---|---|---|---|---|
| 1 | 34.9 | 36.3 | 38.8 | 31.3 | 35.33 | 3.1309 |
| 2 | 32.3 | 31.5 | 33.3 | 41.2 | 34.58 | 4.4776 |
| 3 | 43.1 | 31.5 | 37.0 | 25.0 | 34.15 | 7.7238 |
| 4 | 20.3 | 22.8 | 22.7 | 22.2 | 22.0 | 1.1633 |

Treatments
1. Strain 251 Myconematicide ($1 \times 10^7$–$1 \times 10^8$ spores/ml) + chicken manure.
2. Strain 251 Myconematicide tuber dip.
3. FURADAN 3G (FMC Corporation).
4. Untreated control.

TABLE 12

Changes in soil cyst counts (*Globodera* spp.) during the field trial summarized in Table 11 and expressed as percentages of pretreatment numbers.

| Treatment | After 4 weeks | After 12 weeks |
|---|---|---|
| 1 | 36.8% | 42.0% |
| 2 | 40.4% | 35.1% |
| 3 | 46.2% | 44.5% |
| 4 | 113.7% | 120.0% |

Wherein the percentages reflect the percentage numbers of soil cyst counts in comparison with the pretreatment numbers.

TABLE 13

Effects of different treatments on potato yields expressed as Kg/10 m², potato variety Isola. Sayangan, Atok, Philippines February to June, 1985. Soil infested with *Pratylenchus* spp.

| Treatment | Replicates | | | | | | | | Mean | Standard Error |
| | I | II | III | IV | V | VI | VII | VIII | | |
|---|---|---|---|---|---|---|---|---|---|---|
| 1 | 21.8 | 21.5 | 21.7 | 21.0 | 24.0 | 21.2 | 20.7 | 20.3 | 21.53 | 1.1209 |
| 2 | 25.7 | 18.7 | 20.3 | 21.3 | 19.2 | 20.2 | 20.7 | 22.0 | 21.01 | 2.1690 |
| 3 | 21.2 | 19.3 | 24.3 | 21.3 | 19.0 | 20.2 | 20.0 | 20.0 | 20.66 | 1.6750 |
| 4 | 14.3 | 13.5 | 11.3 | 10.8 | 9.5 | 15.3 | 12.0 | 11.7 | 12.30 | 1.9265 |

Treatments
1. Strain 251 Myconematicide ($1 \times 10^7$–$1 \times 10^8$ spores/hill) + chicken manure.
2. Strain 251 Myconematicide tuber dip.
3. FURADAN 3G.
4. Untreated control.

TABLE 14

Changes in nematode counts during field trial summarised in Table 13 and expressed as percentages of pretreatment populations. *Pratylenchus* spp. accounts for more than 90% of plant parasitic soil nematodes present in all counts.

| Treatment | After 4 weeks | After 12 weeks |
|---|---|---|
| 1 | 39.0% | 29.4% |
| 2 | 30.9% | 30.0% |
| 3 | 42.8% | 43.9% |
| 4 | 132.6% | 141.4% |

Wherein the percentages reflect the percentage numbers of soil cyst counts in comparison with the pretreatment numbers.

EXAMPLES 11 AND 12

Following early indications from the field experiments described in Examples 7 and 8 that the myconematicide would effectively control nematode infestations in banana, semi-commercial trials were initiated on the Marsman Plantation in June 1988 and are scheduled for completion in July 1990. Examples 11 and 12 are results of one such trial available to the end of May 1990.

In this trial, in which 4 ha of unirrigated Giant Cavendish bananas were treated with the myconematicidal suspension as described in Examples 9 and 10, applications were made in June 1988, October 1988, April 1989, October 1989 and March 1990. An adjacent stand of banana was treated with an alternation of chemical nematicides, all of which were applied according to the manufacturer's instructions. Their application began three months earlier than the myconematicide and was as follows: FURADAN® (Carbofuran, FMC Corporation), March 1988; MIRAL (Isazophos, CIBA-GEIGY), August 1988; FURADAN®, January 1989, MIRAL, June 1989; MOCAP (O-Ethyl-S,S-dipropylphosphorodithioate, RHONE-POULENC), November 1989.

Figure 3:
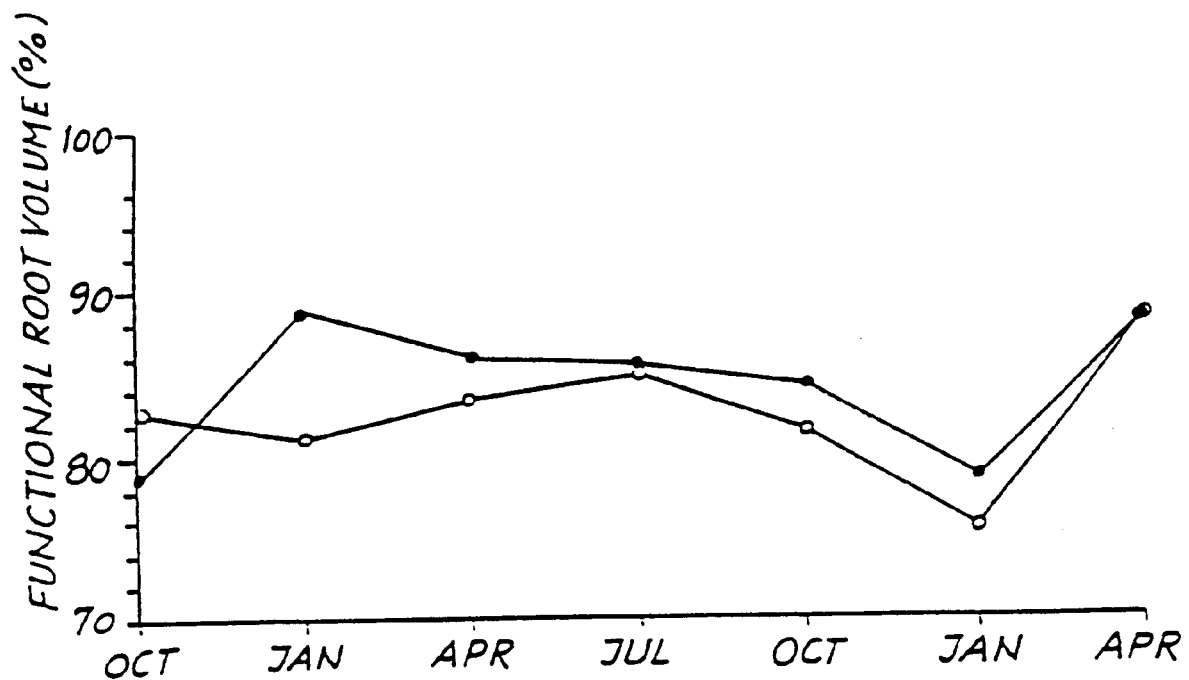
FIG. 3. Quarterly changes in functional root volume from October 1988 to April 1990. Upper, thinner line chemical is nematicides; lower line=myconematicide.

FIG. 3 shows quarterly changes in functional root volume from October 1988 to April 1990. Each data point is the mean of 12 replicates. Explanation of myconematicidal treatment and measurements given previously in discussion of examples 9 and 10. Although initially the chemical nematicide treatment gave a better result than the myconematicide, by April 1990 they are comparable.

Figure 4:
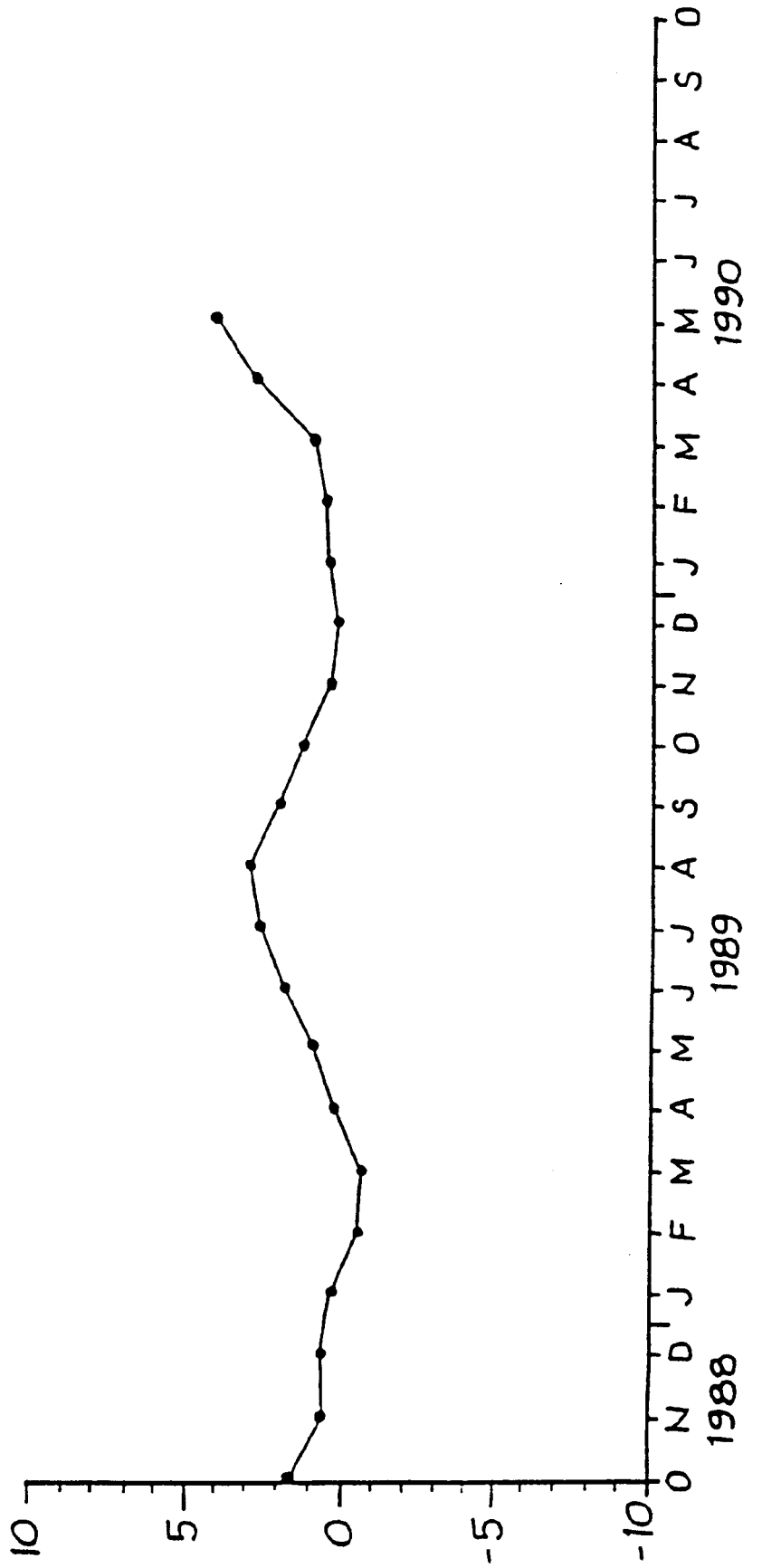
FIG. 4. Changes over time in difference in mean bunch weight between chemically treated bananas and those in which the myconematicide was used. The mean weight of the chemically treated bananas was subtracted from that for the myconematicide treatment.

FIG. 4 shows a time series of comparative mean monthly bunch weight through the trial from October 1988 to May 1990. Data collected as explained in Examples 7 and 8. For each month the mean bunch weight of the chemically treated bananas was subtracted from that calculated for the myconematicide treated bananas. A trend in the positive direction shows that the myconematicide is performing better than the chemical nematicides.

The production figures for this semi-commercial trial indicate that the myconematicide performs at least as effectively as an alternation of chemical nematicides in controlling nematodes in banana.

We claim:

1. A method for controlling nematode infection in a plant crop comprising applying to the crop an amount of infective spores of at least one strain of *Paecilomyces lilacinus* selected from the group consisting of *Paecilomyces lilacinus* 251 (AGAL 89/030550), *Paecilomyces lilacinus* 252 (AGAL 90/028188A), *Paecilomyces lilacinus* 253 (AGAL 90/028188B), and *Paecilomyces lilacinus* 254 (AGAL 90/028188C), the amount being effective to control the nematode infection.

2. A method as claimed in claim 1 wherein the crop is selected from banana, tomato and cotton.

3. A method as claimed in claim 1 wherein the *Paecilomyces lilacinus* strain is applied to the plant crop adjacent to its roots.

4. A myconematicide composition comprising, as an active agent, spores of at least one strain of *Paecilomyces lilacinus* selected from the group consisting of *Paecilomyces lilacinus* 251 (AGAL 89/030550), *Paecilomyces lilacinus* 252 (AGAL 90/028188A), *Paecilomyces lilacinus* 253 (AGAL 90/028188B), and *Paecilomyces lilacinus* 254 (AGAL 90/028188C) in an amount effective to control nematode infection.

5. A myconematicide composition as claimed in claim 4 in which the spores are associated with a carrier and are present on the carrier at a concentration of between $1 \times 10^5$ and $1 \times 10^{10}$ spores per gram of carrier.

6. A biologically pure culture of *Paecilomyces lilacinus* 251 (AGAL 89/030550).

7. A biologically pure culture of *Paecilomyces lilacinus* 252 (AGAL 90/028188A).

8. A biologically pure culture of *Paecilomyces lilacinus* 253 (AGAL 90/028188B).

9. A biologically pure culture of *Paecilomyces lilacinus* 254 (AGAL 90/028188C).

* * * * *